United States Patent
Sjoquist (10) Patent No.: US 10,736,725 B2
(45) Date of Patent: Aug. 11, 2020

(54) IMPLANTS, TOOLS, AND METHODS FOR TREATING PELVIC CONDITIONS

(71) Applicant: Boston Scientific Scimed, Inc., Maple Grove, MN (US)

(72) Inventor: Scott L. Sjoquist, Minnetonka, MN (US)

(73) Assignee: Boston Scientific Scimed, Inc., Mpale Grove, MN (US)

( * ) Notice: Subject to any disclaimer, the term of this patent is extended or adjusted under 35 U.S.C. 154(b) by 228 days.

(21) Appl. No.: 14/775,183

(22) PCT Filed: Mar. 11, 2014

(86) PCT No.: PCT/US2014/023362
§ 371 (c)(1),
(2) Date: Sep. 11, 2015

(87) PCT Pub. No.: WO2014/159389
PCT Pub. Date: Oct. 2, 2014

(65) Prior Publication Data
US 2016/0022403 A1    Jan. 28, 2016

Related U.S. Application Data

(60) Provisional application No. 61/783,930, filed on Mar. 14, 2013.

(51) Int. Cl.
*A61F 2/00*    (2006.01)
*A61B 17/04*   (2006.01)
*A61B 17/00*   (2006.01)

(52) U.S. Cl.
CPC ........ *A61F 2/0063* (2013.01); *A61B 17/0401* (2013.01); *A61F 2/0045* (2013.01);
(Continued)

(58) Field of Classification Search
CPC ........ A61F 2002/0072; A61F 2230/006; A61F 2230/0093; A61F 2/0045; A61F 2/0063
See application file for complete search history.

(56) References Cited

U.S. PATENT DOCUMENTS

| 8,109,867 B2 * | 2/2012 | Rosenblatt ............ A61F 2/0063 600/30 |
| 2003/0114866 A1 | 6/2003 | Ulmsten et al. |

(Continued)

FOREIGN PATENT DOCUMENTS

| EP | 2767258 A1 | 8/2014 |
| WO | 2008079271 A1 | 7/2008 |

(Continued)

OTHER PUBLICATIONS

Extended European Search Report for European Application No. 14774848.7, dated Oct. 7, 2016, 6 pages.

(Continued)

*Primary Examiner* — Christine H Matthews
(74) *Attorney, Agent, or Firm* — Brake Hughes Bellermann LLP (57) ABSTRACT

Described are various embodiments of surgical procedures, systems, implants, devices, tools, and methods, useful for treating pelvic conditions in a male or female, the pelvic conditions including incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, the devices and tools including devices and tools for anchoring an implant to tissue.

21 Claims, 5 Drawing Sheets

(52) U.S. Cl.
CPC ............... *A61B 2017/00805* (2013.01); *A61B 2017/0417* (2013.01); *A61B 2017/0464* (2013.01); *A61F 2002/0072* (2013.01); *A61F 2230/0069* (2013.01); *A61F 2230/0071* (2013.01)

(56) References Cited

U.S. PATENT DOCUMENTS

| | | |
|---|---|---|
| 2005/0277806 A1 | 12/2005 | Cristalli |
| 2006/0195011 A1* | 8/2006 | Arnal ............... A61B 17/06066 600/37 |
| 2007/0156175 A1* | 7/2007 | Weadock ........... A61B 17/0401 606/216 |
| 2010/0234672 A1* | 9/2010 | Weiser ............. A61B 17/00234 600/30 |
| 2010/0261955 A1* | 10/2010 | O'Hern .............. A61B 17/0401 600/37 |
| 2011/0237864 A1 | 3/2011 | Martin et al. |
| 2011/0105836 A1 | 5/2011 | Miller |
| 2012/0259166 A1 | 10/2012 | Karapasha et al. |
| 2014/0228625 A1* | 8/2014 | Crabb ................... A61F 2/0009 600/37 |

FOREIGN PATENT DOCUMENTS

| | | | |
|---|---|---|---|
| WO | 2009044394 A2 | 4/2009 | |
| WO | 2012054985 A1 | 5/2012 | |
| WO | WO 2013009834 A1 * | 1/2013 | ......... A61B 17/0401 |

OTHER PUBLICATIONS

First Examination Report for Australian Application No. 2014240636, dated Sep. 5, 2017, 4 pages.

* cited by examiner

IMPLANTS, TOOLS, AND METHODS FOR TREATING PELVIC CONDITIONS

CROSS-REFERENCE TO RELATED APPLICATIONS

This application claims the benefit from International Application No. PCT/US2014/023362, filed Mar. 14, 2013, which in turn claims priority under 35 USC § 119(e) from U.S. Provisional Patent Application No. 61/783,930, filed Mar. 14, 2013 and titled "IMPLANTS, TOOLS, AND METHODS FOR TREATING PELVIC CONDITIONS", the disclosures of which are incorporated herein by reference in its entirety in their entireties.

TECHNICAL FIELD

The present invention relates generally to devices, systems, and methods for treating pelvic conditions by use of a pelvic implant to support pelvic tissue. The pelvic treatments can include, for example, treatment of vaginal prolapse, e.g., vaginal vault prolapse, by laparoscopic, abdominal, and transvaginal procedures.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions that affect the pelvic floor. Pelvic disorders such as these can result from weakness or damage to normal pelvic support systems. Common etiologies include childbearing, removal of the uterus, connective tissue defects, prolonged heavy physical labor and postmenopausal atrophy.

In more particularity, pelvic floor disorders include cystocele, rectocele, and prolapse such as anal, uterine, and vaginal vault prolapse. Vaginal vault prolapse is a condition that occurs when the upper portion of the vagina loses its normal shape and moves downwardly into the vaginal canal. In its severest forms, vaginal vault prolapse can result in the distension of the vaginal apex outside of the vagina. Vaginal vault prolapse may occur alone, such as can be caused by weakness of the pelvic and vaginal tissues and muscles, or can be associated with a rectocele, cystocele, or enterocele. A rectocele is caused by a weakening or stretching of tissues and muscles that hold the rectum in place, which can result in the rectum moving from its usual location to a position where the rectum presses against the back wall of the vagina. A cystocele is a hernia of the bladder, usually into the vagina and introitus. An enterocele is a vaginal hernia in which the peritoneal sac containing a portion of the small bowel extends into the rectovaginal space.

It is known to treat vaginal vault prolapse by suturing the vaginal vault (e.g., by stitches) to the supraspinous ligament, or by attaching the vaginal vault through mesh or fascia to the sacrum or another posterior location. Generally, these treatments include, abdominal sacralcolpopexy (SCP), which may be performed laparoscopically, and transvaginal sacralcolpopexy (TSCP), wherein these procedures are performed using a variety of different instruments, implants, and surgical methods. Sacral colpopexy involves extending an implant (e.g., a "Y-sling" or "Y-mesh") between tissue to be supported (e.g., tissue of a vaginal vault) and supportive tissue (e.g., tissue at a posterior pelvic region such as at a region of sacral anatomy). The implant is secured to the vaginal tissue at one end and to supportive tissue at another end, to provide therapeutic support for the supported tissue. Implants for these procedures are known, as described and illustrated at Applicant's co-pending application having U.S. Publication No. 2012/0022318, filed Oct. 4, 2011, by Thierfelder et al., entitled IMPLANTABLE ARTICLE AND METHOD, the entirety of which is incorporated herein by reference. These and similar procedures can involve relatively lengthy surgical procedure times and recovery periods.

There is ongoing need in obtaining improved, e.g., minimally invasive, safe, effective and efficient, methods for treating pelvic conditions including incontinence, vaginal prolapse (e.g., vaginal vault prolapse), and other pelvic organ prolapse conditions.

SUMMARY

Tools, systems, and methods as described herein can be used to treat vaginal prolapse conditions (including various forms such as enterocele, cystocele, rectocele, apical or vault prolapse, uterine descent, etc.), and other conditions caused by muscle and ligament weakness, hysterectomies, and the like. In accordance with the invention, sacral colpopexy installation procedures can be performed through an abdominal opening, laparoscopically, or transvaginally, which procedures will require different approaches, each of which can use certain embodiments of devices and methods of the invention.

Certain described devices and methods involve fixation or attachment devices ("anchors") and related methods for placing a pelvic implant, and methods for treating vaginal prolapse (including various forms such as enterocele, cystocele, rectocele, apical or vault prolapse, uterine descent, etc.), and other conditions caused by muscle and ligament weakness. Embodiments of the implants can include a tissue support portion, an extension portion, and one or more anchor (e.g., soft tissue anchor).

As opposed to previous implants useful for treating vaginal prolapse, which are adapted to engage and conform to an outer surface of vaginal tissue, implants as described herein can include a support portion (tissue support portion) that is adapted to be placed to contact at an interior surface of a vagina, a location within the thickness of the tissue of the vaginal wall, or a location of vaginal mucosa adjacent to the tissue of the vaginal wall. The support portion can be shaped and sized to support the vaginal tissue (e.g., tissue of a vaginal vault) in a position that approximates a natural state of the vaginal tissue.

The support portion can also be compressible, meaning that the support portion can be compressed to allow the support portion to achieve small dimensions to allow the support portion to be introduced into a surgical site by a method that is transvaginal or (preferably) by a transabdominal method through a laparoscopic trocar or cannula. Examples of certain compressed implants can be placed laparoscopically in a compressed state at a desired location of vaginal tissue (e.g., at an internal surface of the vaginal tissue), without the need for a vaginal incision in the form typically used for a transvaginal SCP procedure. Once placed at an interior of the vagina, the implant can then be allowed to relax and assume a non-compressed state that is sized and shaped to support the vaginal tissue by attachment to supportive tissue through an elongate attachment (e.g., extension) portion of the implant.

Exemplary support portions are shaped and self-supporting. Exemplary self-supporting shaped tissue support portions can be made of implant material that is less flexible and less conformable (i.e., more rigid, yet still compressible to a necessary degree) compared to previous flexible and conformable implant materials made of mesh and cadaveric material adapted to be attached to an external surface of the vagina. Exemplary self-supporting shaped tissue support portions can be sized and shaped to contact an inner surface of, to fit, and to support, posterior vaginal tissue.

In one aspect, the invention relates to an implant that includes a tissue support portion and an extension portion. The tissue support portion is a shaped self-supporting tissue support portion that includes a surface adapted to engage vaginal tissue at an interior surface of the vaginal tissue, or at a location within the vaginal tissue (wall), to support the vaginal tissue.

In another aspect, the invention relates to a method of placing an implant to support pelvic tissue. The method includes providing an implant that includes a tissue support portion and an extension portion. The tissue support portion is a shaped self-supporting tissue support portion that includes a surface adapted to engage vaginal tissue at an interior surface of the vaginal tissue, or at a location within the vaginal tissue (wall), to support the vaginal tissue. The method includes placing the surface of the self-supporting shaped tissue support portion in contact with an interior surface of vaginal tissue, or at a location within a wall of the vaginal tissue, and extending the extension portion from the vaginal tissue to a region of a sacral component.

BRIEF DESCRIPTION OF THE DRAWINGS

The present invention will be further explained with reference to the appended figures, wherein like structure is referred to by like numerals throughout the several views, and wherein.

All drawings are schematic and not to scale.

DETAILED DESCRIPTION

Methods, devices, and systems as described can be useful in procedures for supporting vaginal tissue, especially posterior vaginal tissue. These methods, devices, and systems can be useful for procedures that include sacral colpopexy procedures (e.g., transvaginal, laparoscopic, and abdominal), along with procedures for treating vaginal vault prolapse caused by rectocele, cystocele, enterocele, and other causes.

Past sacral colpopexy procedures for providing vaginal vault suspension include methods that use an implant, such as a strip of mesh or other material, that attaches on an outer surface of posterior vaginal tissue (e.g., a vaginal cuff or vaginal vault). An elongate attachment portion extends from the posterior vaginal tissue to a region or component of sacral anatomy such as the sacrum (bone itself), a nearby soft supportive tissue such as a sacrospinous ligament, uterosacral ligament, or anterior longitudinal ligament at the sacral promontory. The attachment portion may be secured to the region or component of sacral anatomy using a bone screw, soft tissue anchor, suture, or another fastener useful to connect the implant to tissue of a component of sacral anatomy. The implant can be commercially pre-formed, or may be prepared, assembled, customized or modified by a surgeon. In certain past sacral colpopexy procedures that also involve a hysterectomy, an implant may be attached to an outer surface of posterior vaginal tissue that remains after removal of the uterus and cervix, and also to anatomy to support the vaginal tissue at or around the sacrum, such as to uterosacral ligaments or to the sacrum itself (i.e., to a component of the sacral anatomy). Important to these methods is that the portion of implant that attaches to the vaginal tissue is sufficiently flexible and conformable to be placed over and about the posterior vaginal tissue, and attached to the tissue. Flexible, non-self-supporting mesh is a common implant material used for a portion of implant attached to the vaginal tissue. Also important is the requirement that the flexible and conformable implant material be secured to the exterior tissue of the vagina, e.g., usually by a suture or comparable mechanical fastener.

Implants and methods of the present description include certain features analogous to these past devices and method, such as the use of an implant that extends from vaginal tissue, in a posterior direction, for attachment at supportive tissue (e.g., a region or component of sacral anatomy). An elongate attachment portion, e.g., "extension portion" can be secured to the supportive tissue by any of a bone anchor, a soft tissue anchor, or another mode of supporting the implant to support the vaginal tissue.

Different from previous devices and methods, the presently described devices (implants) and methods involve a tissue support portion that can be placed at an interior surface of the supported vaginal tissue, or at a location within the tissue (within the thickness of the tissue and not at an inner or outer surface); examples of implants do not require the tissue support portion to be attached at an outer surface of the vaginal tissue.

Useful implants can include a tissue support portion adapted to contact, connect to, and support pelvic tissue such as vaginal tissue, along with one or more extension portions connected to the tissue support portion. During use, the tissue support portion can be placed in contact with tissue to be supported, e.g., vaginal tissue. Optionally the tissue support portion may be secured to the vaginal tissue, such as by use of sutures, adhesive, or other attachment means; according to certain embodiments of implants and methods, there is no requirement to attach the support portion to the supported vaginal tissue, and a step of attachment can be specifically excluded. An implant of this type can additionally include one or more extension portions attached to the tissue support portion. Optionally a tissue fastener (e.g., a soft tissue anchor or self-fixating tip) can be used at an end of an extension portion to attach the extension portion to supportive tissue.

Tissue support portions of previous implants used for treating vaginal prolapse have been adapted to contact an external surface of vaginal tissue, to be attached to the external surface, and to be supported by the extension portion of the same implant to thereby support the vaginal tissue attached to the tissue support portion. For typical such previous implants useful to support vaginal tissue, the tissue support portion has been prepared from one or a combination of flexible and conformable sheet-type implant materials; the flexible and conformable nature of these previously-used sheet-type implant materials allows an implant material to be placed externally onto the vaginal tissue to conform to the outer surface for attachment at the outer surface. These flexible and conformable sheet materials have included sheets of biologic materials (e.g., porcine and cadaveric tissue), mesh, and other materials or combinations of materials that are flexible and able to conform to and to be secured to an outer surface of vaginal tissue.

Tissue support portions of implants described herein can differ from past tissue support portions that are flexible, conformable, and adapted to be placed at exterior vaginal tissue. Certain embodiments of tissue support portions of implants described herein can be made of materials that are different from the usual flexible and conformable mesh and biologic materials of past implants. Described tissue support portions may be less flexible and more rigid than mesh and biologic implant materials used in past implants, and are shaped to support vaginal tissue as opposed to being conformable to the vaginal tissue. Optionally or in addition, described tissue support portions may be specifically shaped to contact portions or areas of vaginal tissue other than an exterior surface (as previous implants are designed to contact), e.g., may be specifically shaped to contact an inner surface of the vaginal tissue to be placed within the tissue.

Past implants for supporting vaginal tissue have include support portions made of flexible and conformable implant materials that are designed to and capable of conforming to an outside surface of the vaginal tissue. Examples of these flexible and conformable implant materials include flexible and conformable polymeric mesh materials and flexible biologic materials such as cadaveric and porcine materials. In contrast, the present implants include a support portion that is shaped, i.e., "pre-shaped," to fit to and support vaginal tissue without substantially conforming to the tissue; the vaginal tissue fits around, conforms to, and becomes supported by the shape of the shaped support portion. The shape of the shaped support portion may be three-dimensionally curved in the form of a partial sphere (e.g., a "cup" or "bowl" shaped support portion), or a partial cylinder or tube, or may be of another two- or three-dimensionally curved surface that approximates a shape of vaginal tissue to be supported, such as a three-dimensional inner surface of vaginal tissue; alternately or in addition, the shape may be flat or planar, or may include a flat, planar, or angled surface in combination with a curved portion.

The shaped support portion may derive its shape due to a material of the support portion, a treatment of the support portion, or by the use of any other shape-forming forming or shape-retaining material, process, or technique. A shape may be imparted to a shaped support portion by any mode of shaping, such as by heat setting or application of a stiffening coating, by molding, or by including one or more stiffening material (e.g., a support, frame, etc.) in or on an the material of the support portion. The shaping desirably produces a shaped support portion that exhibits a resilient yet biased (e.g., semi-rigid) form or shape such as a three-dimensional form that approximates a surface of vaginal tissue to be supported. In a relaxed state the shaped implant will retain the three-dimensional form, but that form could be stressed and deformed partially by application of an opposing force (e.g., the weight of supported tissue) on the shaped implant.

In more detail, a shaped support portion may be treated to form a stiffened, non-flat shape by any desired method, such as by thermoforming, heat treating, molding, or by application of a polymeric or non-polymeric stiffening coating. The coating may be any bio compatible polymeric or non-polymeric coating material, and may be bioresorbable or non-bioresorbable. A stiffening coating can be applied using any suitable source and method to coat an otherwise more flexible implant material (e.g., a mesh or biologic material) for stiffening and shaping into a stiffened, biased, non-flat, non-planar, three-dimensional form.

A shaped support portion may also exhibit its shape due to the material of the implant. A material that is more stiff than a standard flexible and conformable mesh of a mesh implant may be useful to form a shaped support portion. For example, a shaped support portion may be made of a molded stiff plastic or other polymer such as a polyolefin (e.g., polypropylene), nylon, or silicone, or may be made of an even more rigid material such as a metal, e.g., a woven metal screen-type material, or a metal sheet. Any of these materials can be fenestrated if desired to allow for tissue in-growth after placement.

A shaped support portion is also self-supporting, meaning that the support portion can be generally less flexible than previous flexible and conformable (mesh or biologic) implant materials, but is not entirely inflexible and may be sufficiently flexible (meaning not entirely rigid) to be compressed into a non-relaxed form that has dimensions that allow the compressed support portion to be inserted laparoscopically to a surgical site, e.g., in a coiled, folded, or otherwise compressed form. During use, when vaginal tissue is placed in contact with a self-supporting shaped support portion as described, the tissue will conform to the support portion to an extent greater than the extent to which the support portion conforms to the tissue; the support portion is less conformable to the vaginal tissue than the vaginal tissue is conformable to the support portion.

A shaped support portion can be considered to be "self-supporting," for example, if the support portion will substantially maintain its shape (whether planar, curved, a combination thereof, or otherwise non-planar) under at least the force of its own weight. A flexible and conformable implant material such as a mesh or biologic material used previously for implants used to treat pelvic organ prolapse will be flexible and conformable to the extent that a typical flexible and conformable implant material is non-self-supporting; many flexible and conformable implant materials will lie flat on a planar surface, will adapt a curved form of a curved surface, or will hang under its own weight if supported at an edge. In contrast, a self-supporting shaped support portion as described will be self-supporting in a given shape; a curved or flat shaped support portion will maintain a shape of its curved or flat surface if supported by a surface having form different from the curved or shaped form of a particular support portion, or if held at an edge of the support portion.

To facilitate placement at a surgical site, especially through a narrow surgical opening (e.g., laparoscopically, trans-vaginally, or trans-urethrally) an self-supported shaped tissue support portion may have two configurations: a relaxed (non-compressed, stable) configuration, and an non-relaxed (e.g., compressed, coiled, folded, or unstable) configuration. The tissue support portion may be inserted into a patient when configured in the non-relaxed or compressed configuration to minimize size and invasiveness. In this compressed configuration, for example, the support portion may be coiled, folded, rolled, or otherwise compressed to a size that allows passage of the support portion through a cannula or trocar used in a laparoscopic surgical procedure, or to a size that allows passage of the implant transvaginally. Once placed at a desired surgical location adjacent to vaginal tissue, the support portion in the compressed configuration can be allowed to open to the non-compressed stable configuration, which exhibits a shape useful to support the vaginal tissue.

Optionally, a support portion may acquire or regain a relaxed (stable) configuration by being made of a material such as nitinol that can change shape upon being exposed to different temperatures or being held in an unstable configuration by a constraining structure such as a sheath. To produce a support portion as described and capable of achieving and alternating between the relaxed and the non-relaxed states, the support portion may alternately be made from a different bio-compatible material such as polypropylene, silicone, or another implant grade plastic; a metal such as stainless steel, titanium, nitinol; or a combination thereof. The support portion may be a solid piece of material in the form of a sheet or a three dimensional structure having a thickness greater than a sheet-type mesh or biologic implant material; the support portion may include holes or other fenestrations to promote tissue ingrowth, prevent migration, and prevent tissue erosion. Holes, if present, may be all the same size or of different sizes and may be regularly or irregularly spaced.

A support portion may be attached to a surface of vaginal tissue to be supported using any of various useful surgical techniques methods. As one example, a surface of a support portion may be contacted and adhered to a surface of vaginal tissue by use of an adhesive, e.g., a biologic adhesive, one example being hydrosilk. Alternately or additionally, a support portion may be sutured to supported vaginal tissue by use of absorbable or non-absorbable sutures. Certain embodiments of methods do not require a support portion to be attached to vaginal tissue by a suture or adhesive, and can specifically exclude a step of attaching the support portion to vaginal tissue by use of a suture or adhesive.

An implant that includes a self-supported shaped support portion as described can also include an extension portion attached to the shaped support portion. An extension portion can be an elongate segment or portion of the implant that extends from the tissue support portion and is useful to pass through or attach to tissue of the pelvic region to thereby provide support for the tissue support portion and the supported vaginal tissue. Extension portions are elongate pieces of material (e.g., mesh, suture, or biologic material) that extend from the tissue support portion and either are or can be connected to the tissue support portion, and are useful to attach to anatomical features or "supportive tissue" in the pelvic region (e.g., using a self-fixating tip or another form of tissue fastener) to thereby provide support for the tissue support portion and the supported tissue. The supportive tissue may be bone or a soft tissue such as muscle, fascia, ligament, tendon, or the like. For treating vaginal vault prolapse, or more extension portions can extend from a tissue support portion adapted for placement in contact with vaginal tissue, as described, in a generally posterior direction for attachment to tissue in a pelvic region, such as by extending through a tissue path or space of a pelvic region to an internal anchoring point (for attachment by bone anchor, tissue fastener, etc.), or to an external incision.

An extension portion can be attached to supportive tissue by any previous or yet-to-be developed attachment mechanism or device, e.g., by any bone anchor, soft tissue anchor tissue fastener, or the like, useful to secure the extension portion to supportive tissue. A distal end of an extension portion can include or be adapted to engage a tissue fastener for attaching the extension portion to supportive tissue. The tissue fastener can be, e.g., a soft tissue anchor, a self-fixating tip, a biologic adhesive, a tissue clamp, opposing male and female connector elements that securely engage when pushed together, or any other device to secure a distal end of an extension portion to tissue of the pelvic region.

The implant may also have extension portions that do not include a tissue fastener at a distal end of an extension portion, for example if the distal end is designed to be secured to tissue by other methods (e.g., suturing). Certain methods, implants, and anchors of the may use a helical anchor such as a screw or coil that can be inserted (e.g., driven) into tissue, preferably soft tissue such as an anterior longitudinal ligament, by rotating about a longitudinal axis upon which the helical anchor advances into the tissue in a longitudinal direction. Other methods may include an anchor in the form of a "self-fixating tip," which can be inserted by pushing the anchor using a straight or curved needle.

Exemplary extension portions can be made of any useful implant material and may be generally shaped and sized according to previous implants useful for treating vaginal prolapse, adapted to extend between vaginal tissue and supportive tissue and to be connected to each of the vaginal tissue and the supportive tissue. An extension portion can include portions or sections that are synthetic (e.g., synthetic mesh such as a polypropylene mesh) or that are made of biological material (e.g., porcine, cadaveric, etc.). An extension portion may be made of a single piece of material or of multiple pieces or layers of material. Exemplary extension portions may be made of materials and exhibit general size and shape features comparable to those of extension portions of previous implants useful for treating vaginal prolapse. Examples of such implants are commercially available from American Medical Systems, Inc., of Minnetonka Minn., under the trade names "Apogee," "Perigee," and "Elevate" for use in treating pelvic prolapse (including vaginal vault prolapse, cystocele, enterocele, etc.). Other examples of extension portions are described as a feature of "Y-sling" implants described at Assignee's co-pending application having U.S. Publication No. 2012/0022318, filed Oct. 4, 2011, by Thierfelder et al., entitled IMPLANTABLE ARTICLE AND METHOD, the entirety of which is incorporated herein by reference.

Dimensions of an implant as described can be as determined to be useful for any particular installation procedure, treatment, patient anatomy, and to support a specific tissue or type of tissue. Exemplary dimensions can be sufficient to allow the tissue support portion to contact posterior vaginal tissue and to allow one or more extension portions to extend from the posterior vaginal tissue to a desired supportive tissue to allow the extension portion to be secured to or pass through tissue of the pelvic region and support the tissue support portion.

Figure 1:
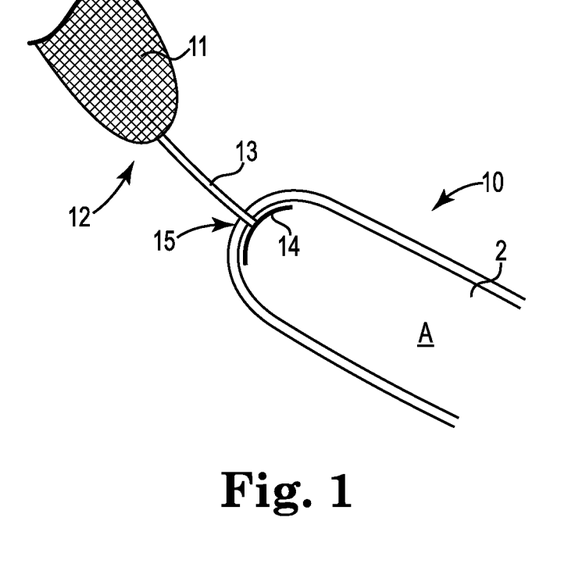
FIG. 1 is a side view of an example placement of the device.
Figure 2:
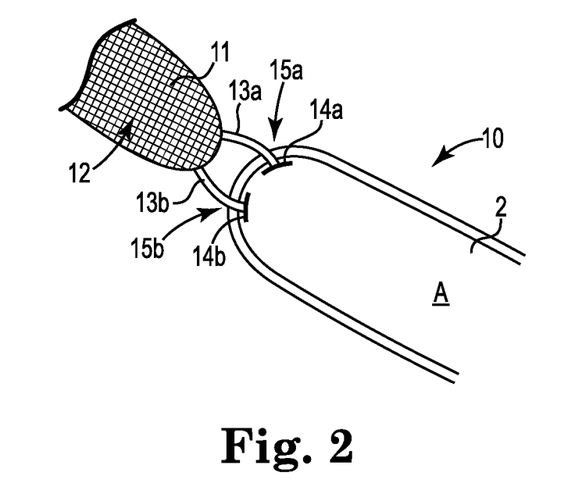
FIG. 2 shows an alternative placement of the device.

Referring now to FIGS. 1 and 2, a method and device are illustrated for delivering an implant as part of a sacral colpopexy procedure. Implant 10 includes extension portion 12 and a self-supporting shaped tissue support portion 14. Extension portion 12 includes mesh portion 11 and elongate connector or connective portion 13, which is of a narrow cross-section to allow connective portion 13 to be passed through vaginal tissue 2 with reduced trauma. A distal end of connective portion 13 is connected to tissue support portion 14. Connector 13 may be made of a material useful to securely connect mesh portion 11 of extension portion 12 to support portion 14; connector 13 may be a flexible plastic strip, suture, etc. Tissue support portion 14 is shaped to reside within the vagina A, and is self-supporting so that support portion 14 will cause the vaginal tissue to conform to the shape of support portion 14. In an example embodiment tissue support portion 14 is configured to anchor within the vagina through a single insertion point 15 passing through a posterior location of vaginal tissue 2 (FIG. 1). In an alternative embodiment, an implant 10 can include more than one self-supporting shaped tissue support portion 14a, 14b, and connectors 13a, 13b, wherein self-supporting shaped tissue support portions 14a, 14b are configured to reside within the vagina through more than one insertion point, for example, two insertion points 15a, 15b (FIG. 2). Tissue support portion 14 (and 14a, 14b) is sized and shaped to support vaginal tissue without the need for suturing or otherwise attaching support portion 14 (and 14a, 14b) to the vaginal tissue.

Implant 10 may be placed as illustrated by inserting implant 10 surgically through a vaginal, abdominal, or laparoscopic incision. In a vaginal approach, at least one incision is made in the vaginal apex, through which extension portion 12 may be passed. In an abdominal approach, an incision is made in the vaginal apex from an exterior side of the vaginal tissue; tissue support portion 14 is then passed from the abdominal cavity into the vaginal interior. In a laparoscopic approach, implant 10 is designed to be capable of passing through a laparoscopic instrument such as a trocar or cannula. Using laparoscopic tools and techniques, implant 10 may be passed into a pelvic region of the posterior vaginal tissue and the sacrum; a distal end of extension portion 12 may be secured to supportive tissue such as an anterior longitudinal ligament; shaped support portion 14 in a compressed state can be passed laparoscopically from an outside of the vagina, through insertion point 15, to an interior of the vagina; upon passing compressed shaped support portion 14 into the interior of the vagina, support portion 14 may be released to a relaxed state and situated to support the posterior vaginal tissue.

Figure 3A:
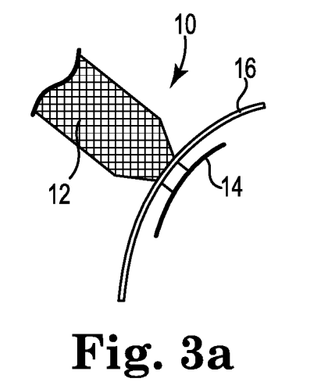
FIGS. 3a-3f illustrate different embodiments of the device.

FIG. 3a illustrates an alternate embodiment of an implant 10, which includes mesh extension portion 12, a first self-supporting shaped tissue support portion 14, and a second self-supporting shaped tissue support portion 16 that is biodegradable. Mesh extension portion 12 is sized and shaped to extend from a region of a sacral component to posterior vaginal tissue (not shown). The distal end of the mesh extension portion 12 is connected directly to first tissue support portion 14 and second (biodegradable) tissue support portion 16. Tissue support portion 14 and biodegradable tissue support 16 may be sized and shaped to contour to the vaginal apex. In use, tissue support portion 14 may be placed to within the vaginal apex in contact with an interior surface of the vagina, while biodegradable tissue support portion 16 may reside external to the vaginal apex. Tissue support portion 14 is designed to provide permanent or semi-permanent support to the vaginal apex. Any of these self-supporting shaped tissue support portions can optionally be compressible, or can otherwise be capable of fitting through a laparoscopic cannula or trocar.

Figure 3B:
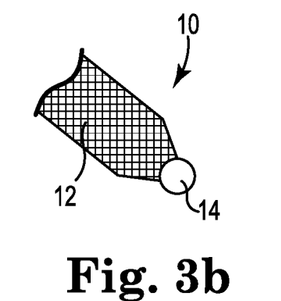
Figure 3C:
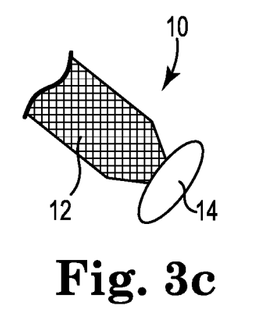
Figure 3D:
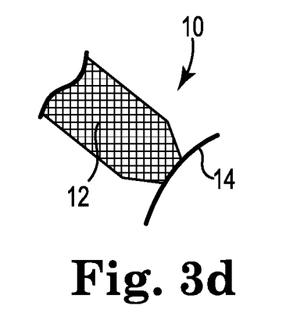
Figure 3E:
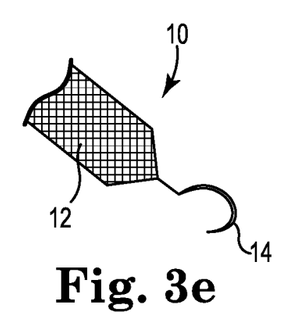
Figure 3F:
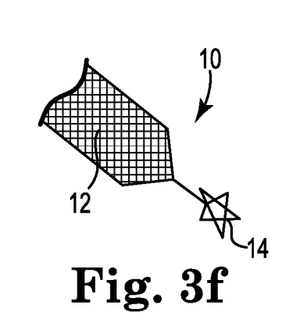

FIGS. 3b-3f show additional embodiments of implants 10. An implant 10 comprises of an extension portion 12 and a self-supporting shaped tissue support portion 14. The tissue support portion 14 is designed to reside within the interior of the vagina to contact and support vaginal apex and provide superior support to vaginal tissue at the apex. Tissue support portion 14 of FIG. 3b is shown as a sphere or ball of polymeric material sized to support a vaginal apex. The tissue support portion of 3c is a substantially planar toggle polymer, while FIG. 3d is a curved toggle. The shape of the toggle may be that of a square, rectangle, circle, triangle, or other shape commonly known in the art. A self-supporting shaped tissue support portion 14, instead of a polymer, may alternately be made from nitinol, such as a complete or incomplete loop (FIG. 3e), a star (FIG. 3f) or any other symmetrical, non-symmetrical, or irregularly-shapes three-dimensional structure capable of being positioned within vaginal tissue, at a vaginal apex, to therapeutically support the vaginal apex and vagina to treat a prolapsed condition.

Figure 4A:
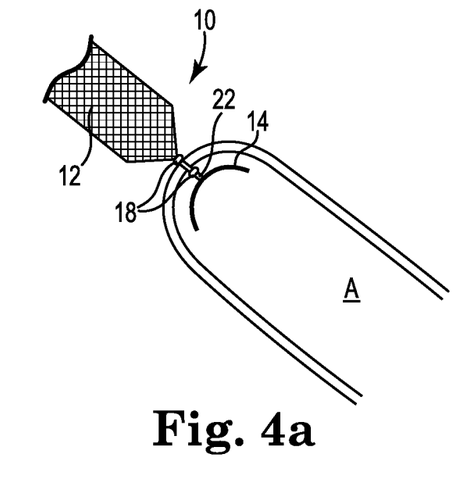
FIGS. 4a-f illustrate alternate embodiments of the device.
Figure 4B:
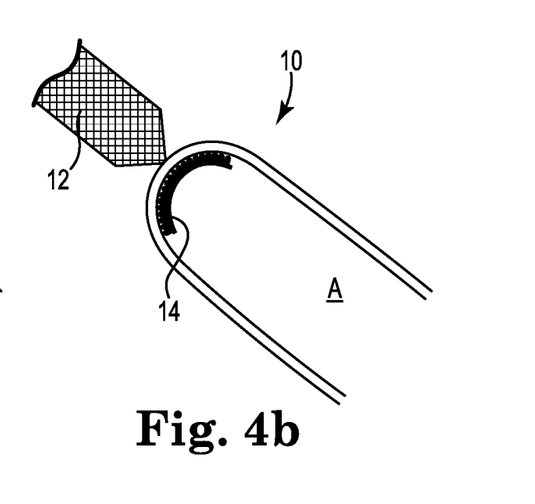

FIGS. 4a-4f illustrate alternative embodiments of the implant 10. FIG. 4a shows an implant 10 with a self-supporting shaped tissue support portion 14 comprising at least one grommet 18 and a tissue support connector 22, connecting mesh extension portion 12 and support portion 14. Grommet 18 can be used to secure tissue support portion 14 to vagina A at a desired distance along the tissue support connector 22 relative to extension portion 12. Grommet 18 may be placed on either side of the vaginal apex as shown in FIG. 4a, or one grommet 18 may be placed on the outside of the vaginal apex. FIG. 4b shows a tissue self-supporting shaped support portion 14 comprising a roughed edge or surface on the vaginal-tissue-surface side of tissue support portion 14. The rough edge or surface may provide for desired or improved tissue ingrowth, less movement of the implant 10, or both. The rough or surface edge may be shaped as a chevron, serpentine, repeating regular extensions such as ridges, diamonds, bumps, apertures, fenestrations, or another similar shape, form, or structure.

Figure 4C:
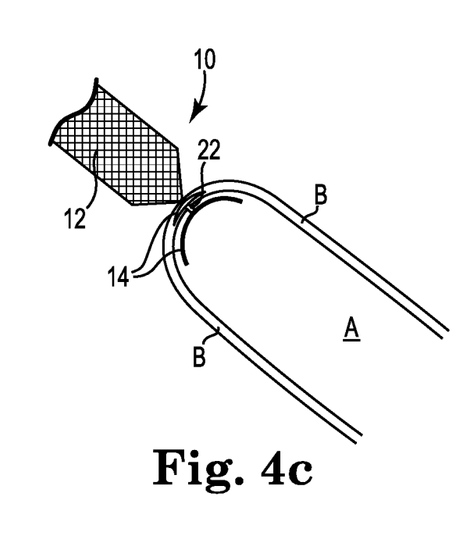

FIG. 4c shows an implant 10 comprising self-supporting shaped tissue support portion 14 that includes a portion adapted to be placed both within the vagina A, and another portion adapted to be placed at vaginal mucosa B or the adjacent vaginal tissue. Tissue support portion 14 comprises at least two pieces, one of which is within the interior space of vagina A, and the other that placed within the vaginal mucosa B (or adjacent vaginal tissue). The self-supporting shaped tissue support portion 14 placed within the vaginal mucosa B (or adjacent vaginal tissue) may be of any shape, such as a flat disc, a tapered disc, a convex or concave disc, a flat square, etc. The two portions of tissue support portion 14 are connected by the tissue support connector 22. The tissue support portion 14 located in the vaginal mucosa or tissue layer may be shaped as an anchor or other like structure capable of being engaging soft tissue mass. The tissue support portion 14 located in the interior space of the vagina may be shaped to contour to the inside surface of the vaginal tissue. The support portion 14 within the interior space of vagina A may be permanent or biodegradable. The support portion 14 within the vaginal mucosal layer B or adjacent tissue may be permanent or biodegradable.

Figure 4D:
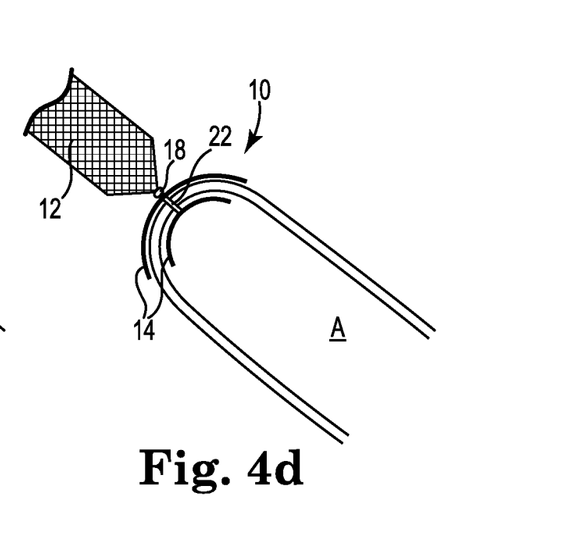

FIG. 4d shows a similar embodiment with the addition of a grommet 18 located on the distal (abdominal) side of the support portion 14, and also including a tissue support portion located on an exterior surface of the vaginal tissue; one self-supporting shaped tissue support portion 14 placed on the interior surface of the vagina, and the second self-supporting shaped tissue support portion is placed on an exterior surface of the vagina.

Figure 4E:
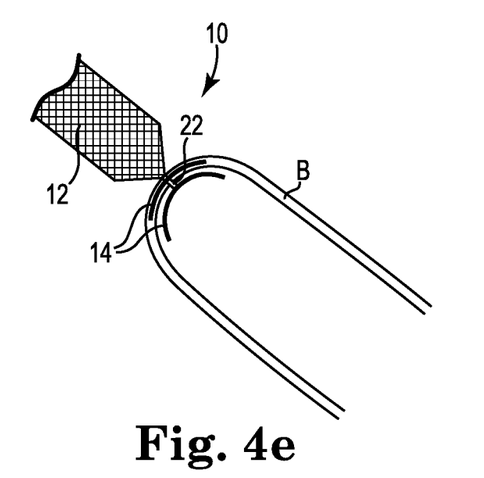

FIG. 4e illustrates yet another similar embodiment of an implant 10 that includes two self-supporting shaped he tissue support portions 14. The tissue support portion 14 may comprise a cup-shaped portion implanted within the vaginal mucosa B or adjacent vaginal tissue. The cup-shaped portion is sized and shaped to contour to the vaginal tissue.

Figure 4F:
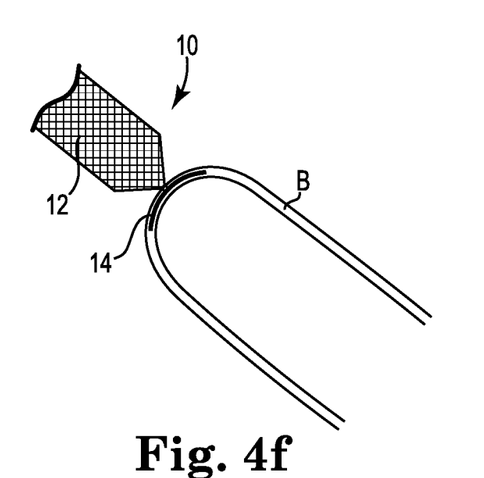

FIG. 4f shows an embodiment of an implant 10, wherein the tissue support portion 14 is located solely within the vaginal mucosa B or adjacent vaginal tissue.

According to exemplary uses of certain described implants, vaginal tissue may be supported by placing an implant using a surgical technique that includes a transvaginal method, a laparoscopic method, or an open surgical method. A self-supported shaped implant as described may be introduced to a location of pelvic tissue by any suitable surgical technique, including transvaginal methods, open abdominal methods, laparoscopic methods (through abdominal tissue), and trans-urethrally. In certain preferred surgical methods, an implant (including a self-supporting shaped tissue support portion) can be compressed, coiled, folded, or otherwise reduced in at least two dimensions to be sized to pass through a lumen of a surgical cannula or trocar, such as a cannula or trocar that can be useful to pass an implant laparoscopically (see FIGS. 5A, 5B, and 5C). In these embodiments, the compressed cross section of a tissue support portion can include dimensions that are in a range from about ⅛ inch to about ¾ inch, e.g., from about ⅛ inch to about ½ inch, or otherwise sufficiently small to pass through a surgical trocar or cannula. Once the compressed tissue support portion and implant are passed to the surgical site, e.g., with the tissue support portion being located at an interior of a vagina, the compressed tissue support portion can be allowed to de-compress, i.e., relax, to its relaxed state. In the relaxed state the implant is able to support the shape and the position of the vaginal tissue; the extension portion can be attached to supportive tissue to additionally support the position of the vaginal tissue and vagina.

Exemplary steps can include:
1—Complete an incision at a desired location for a desired technique; e.g., through the vaginal apex (or posterior to the apex) and the peritoneum for a transvaginal method, or at one or multiple abdominal locations for a laparoscopic method;
2—Introduce an implant or through the incision (e.g., through a laparoscopic trocar or cannula);
3—Confirm sacral promontory (bone=firm feel, promontory=increased depth with minimal anterior movement) (e.g., laparoscopically);
4.—Optionally compress the self-supporting shaped tissue support portion to reduce its dimensions to allow improved passage through the incision or through a laparoscopic trocar or cannula;
5.—Pass the implant through the surgical incision;
6.—Using a soft tissue anchor delivery device (or another suitable fastening device), secure the extension portion of the implant to tissue of the sacral promontory by placing a fastener through the implant and into tissue of the sacral promontory (e.g., laparoscopically or transvaginally);
5.—Place the shaped self-supported tissue support portion at a desired location of vaginal tissue, e.g., at a location interior to the vagina or at a location of vaginal mucosa or adjacent tissue; if the method includes a previous step of compressing the self-supported tissue support portion, this step can involve allowing the self-supported tissue support portion to be released and relax to an uncompressed state;
6—Optionally secure the tissue support portion to the vaginal tissue using, e.g., one or more suture (this step is optional and not required).

As indicated, these steps can be adapted to any of various surgical techniques, including those performed trans-abdominally, laparoscopically, transvaginally, etc.

Figure 5A:
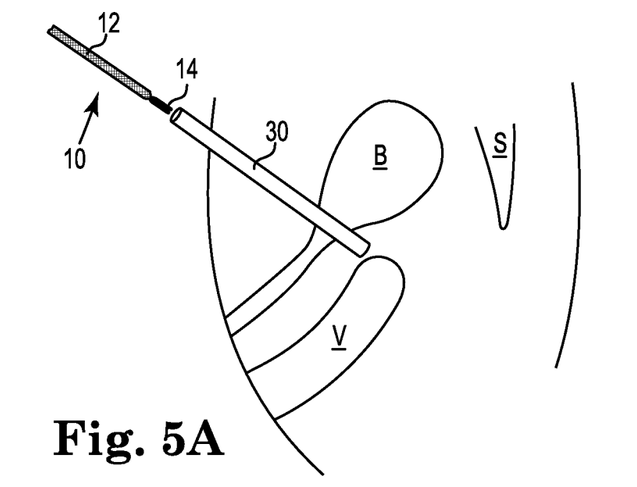
FIGS. 5a, 5b, and 5c illustrate exemplary steps of method as described.
Figure 5B:
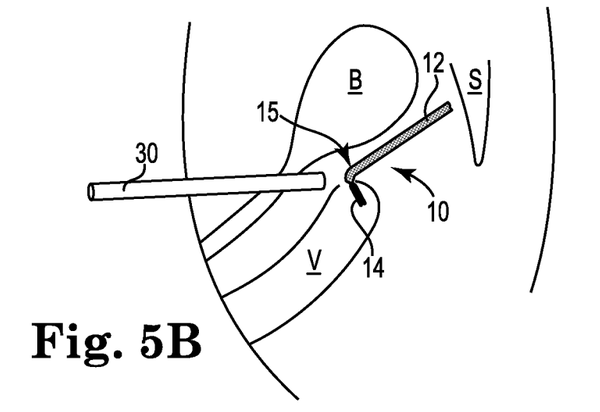
Figure 5C:
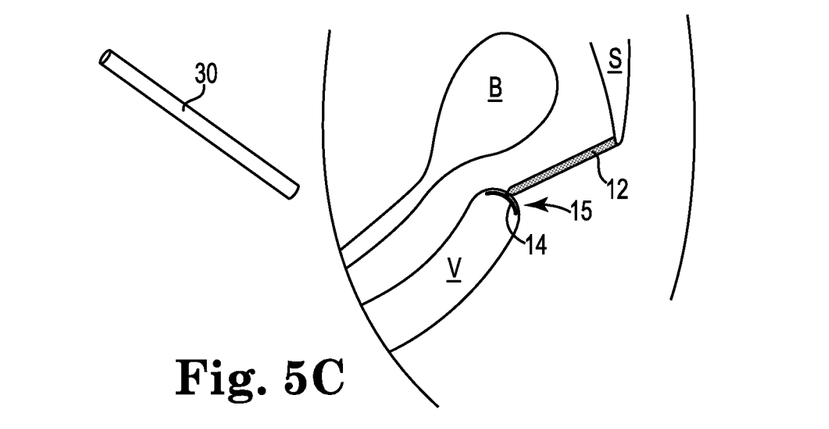

Certain exemplary steps of a laparoscopic method are shown at FIGS. 5A, 5B, and 5C. FIG. 5A shows an example of cannula (or trocar) 30 useful for trans-abdominal laparoscopic surgical techniques. Implant 10 (e.g., as shown at any of the figure of the present description), including self-supporting shaped support portion 14 and extension portion 12, is shown with support portion 14 in a compressed (coiled, folded, or the like) state with dimensions that allow passage of implant 10 through trocar 30. A shown at FIG. 5B, trocar 30 can be placed trans-abdominally to place a distal end at a desired surgical location; implant 10 can be passed internally along the length of trocar 30 to pass extension portion 12 and compressed support portion 14 to a region of a posterior vagina (V), a bladder (B), and a sacrum (S). Extension portion 12 can be attached (e.g., laparoscopically) to sacrum (S) (see FIG. 5C). Support portion 14, in a compressed state, can be passed through an insertion point 15 at a posterior vaginal location and into the interior of the vagina (V), whereupon implant support portion 14 can assume an expanded (non-relaxed) state (see FIG. 5C).

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the references incorporated herein are envisioned for use with the present invention as well. All patents, patent applications, and publications cited herein are hereby incorporated by reference in their entirety as if individually incorporated, and include those references incorporated within the identified patents, patent applications and publications.

The invention claimed is:
1. An implant, comprising:
a plurality of tissue support portions being of a pre-shaped material and configured to support vaginal tissue such that the vaginal tissue conforms to the pre-shaped material when disposed in a patient body;
an extension portion including a mesh material, the pre-shaped material being stiffer than the mesh material, the extension portion including a first end portion and a second end portion, a distance between the first end portion and the second end portion defining a longitudinal line;
a first connecting member configured to pass through the vaginal tissue, the first connecting member being disposed substantially along a same direction as the longitudinal line, the first connecting member having a first end portion and a second end portion, the first end portion of the first connecting member being coupled to one of the plurality of tissue support portions and configured to be disposed in an interior of a vagina, the second end portion of the first connecting member being coupled to an end of the extension portion and being configured to be disposed external of the vagina, and
a second connecting member configured to pass through the vaginal tissue, the second connecting member being disposed substantially along a same direction as the longitudinal line, the second connecting member having a first end portion and a second end portion, the first end portion of the second connecting member being coupled to one of the plurality of tissue support portions and configured to be disposed in the interior of the vagina, the second end portion of the second connecting member being coupled to the end of the extension portion and being configured to be disposed external of the vagina, the second connecting member being adjacent to the first connecting member,
wherein the first connecting member is substantially parallel with the second connecting member.
2. The implant as recited in claim 1, wherein a surface of one of the plurality of tissue support portions includes a curved portion.

3. The implant as recited in claim 1, wherein a shape of one of the plurality of tissue support portions is a sphere.

4. The implant as recited in claim 1, wherein the extension portion is configured to be secured to a region of a sacral component.

5. The implant as recited in claim 1, wherein at least one of the plurality of tissue support portions retains a shape of the surface under a force of weight.

6. The implant as recited in claim 1, wherein at least one of the plurality of tissue support portions is configured to be compressed to a form to fit through a cannula or trocar.

7. The implant as recited in claim 1, wherein at least one of the first connecting member or the second connecting member is a suture.

8. The implant as recited in claim 1, wherein at least one of the first connecting member or the second connecting member includes at least one of a suture or at least one grommet.

9. The implant as recited in claim 1, wherein the pre-shaped material includes a mesh or biologic material coated with a stiffening coating.

10. The implant as recited in claim 1, wherein the pre-shaped material includes a polymer material.

11. The implant as recited in claim 1, wherein at least one of the plurality of tissue support portions is a separately-formed construct from another of the plurality of tissue support portions.

12. The implant as recited in claim 11, wherein the at least one of the plurality of tissue support portions includes a biodegradable material.

13. The implant as recited in claim 1, wherein a surface of at least one of the plurality of tissue support portions includes a plurality of ridges.

14. The implant as recited in claim 1, wherein a surface of at least one of the plurality of tissue support portions is configured to contact an interior surface of the vagina.

15. The implant as recited in claim 1, wherein a surface of at least one of the plurality of tissue support portions is configured to be disposed at a location within the vaginal tissue.

16. The implant as recited in claim 1, wherein a first tissue support portion of the plurality of tissue support portions is configured to engage an outer surface of the vaginal tissue and a second tissue support portion of the plurality of tissue support portions is configured to engage an inner surface of the vaginal tissue.

17. The implant as recited in claim 1, wherein a first tissue support portion of the plurality of tissue support portions has a first size and a second tissue support portion of the plurality of tissue support portions has a second size being different than the first size.

18. The implant as recited in claim 1, wherein each of the plurality of tissue support portion includes a first surface portion and a second surface, opposite the first surface portion, the first surface portion having a first curvature and the second surface portion having a second curvature, the second curvature having a same direction as the first curvature.

19. A method of placing an implant to support pelvic tissue, the method comprising:
providing the implant to a bodily tissue, the implant including:
a plurality of tissue support portions being of a pre-shaped material and configured to support vaginal tissue such that the vaginal tissue conforms to the pre-shaped material when disposed in the bodily tissue;
an extension portion including a mesh material, the pre-shaped material being stiffer than the mesh material, the extension portion including a first end portion and a second end portion, a distance between the first end portion and the second end portion defining a longitudinal line;
a first connecting member configured to pass through the vaginal tissue, the first connecting member being disposed substantially along a same direction as the longitudinal line, the first connecting member having a first end portion and a second end portion, the first end portion of the first connecting member being coupled to one of the plurality of tissue support portions and configured to be disposed in an interior of a vagina, the second end portion of the first connecting member being coupled to an end of the extension portion and being configured to be disposed external of the vagina, and
a second connecting member configured to pass through the vaginal tissue, the second connecting member being disposed substantially along a same direction as the longitudinal line, the second connecting member having a first end portion and a second end portion, the first end portion of the second connecting member being coupled to one of the plurality of tissue support portions and configured to be disposed in the interior of the vagina, the second end portion of the second connecting member being coupled to the end of the extension portion and being configured to be disposed external of the vagina, the second connecting member being adjacent to the first connecting member;
placing a surface of at least one of the plurality of tissue support portions in contact with the vaginal tissue; and
extending the extension portion from the vaginal tissue to a region of a sacral component.

20. The method as recited in claim 19, wherein the method is a method of treating vaginal prolapse in a female patient, the method further comprising:
passing a laparoscopic trocar through an abdominal incision of the patient to place a distal end of the trocar at a location of the vaginal tissue of the patient;
placing the at least one of the plurality of tissue support portions in a compressed state;
passing the at least one of the plurality of tissue support portions in the compressed state through the trocar;
passing the at least one of the plurality of tissue support portions in the compressed state through the vaginal tissue and to an interior of a vagina;
releasing the at least one of the plurality of tissue support portions from the compressed state; and
contacting a surface of the at least one of the plurality of tissue support portions with the vaginal tissue.

21. An implant, comprising:
a tissue support portion including a surface configured to engage vaginal tissue, the tissue support portion including a shape-retaining material, the shape-retaining material being configured to be self-supporting so that the vaginal tissue conforms to a shape of the tissue support portion;
an extension portion including a mesh material, the shape-retaining material being stiffer than the mesh material; and
a connecting member configured to connect the tissue support portion and the extension portion, the connecting member having a suture and at least one grommet, the suture being configured to be disposed at a location within the vaginal tissue, the suture having a first end portion coupled to the tissue support portion and a second end portion coupled to the extension portion, the grommet being disposed between the first end portion of the suture and the second end portion of the suture.

* * * * *